United States Patent
Omura

(10) Patent No.: US 9,165,118 B2
(45) Date of Patent: Oct. 20, 2015

(54) MEDICINE DISPENSING SYSTEM

(75) Inventor: Yoshihito Omura, Tokyo (JP)

(73) Assignee: TOSHO, INC., Tokyo (JP)

( * ) Notice: Subject to any disclaimer, the term of this patent is extended or adjusted under 35 U.S.C. 154(b) by 528 days.

(21) Appl. No.: 13/808,208

(22) PCT Filed: Apr. 13, 2011

(86) PCT No.: PCT/JP2011/059215
§ 371 (c)(1),
(2), (4) Date: Jan. 3, 2013

(87) PCT Pub. No.: WO2012/005039
PCT Pub. Date: Jan. 12, 2012

(65) Prior Publication Data
US 2013/0110282 A1    May 2, 2013

(30) Foreign Application Priority Data

Jul. 7, 2010 (JP) .................. 2010-155288
Jul. 7, 2010 (JP) .................. 2010-155292
Dec. 17, 2010 (JP) .................. 2010-282435

(51) Int. Cl.
*G06F 19/00* (2011.01)
*G07F 17/00* (2006.01)

(52) U.S. Cl.
CPC ........ *G06F 19/3462* (2013.01); *G07F 17/0092* (2013.01)

(58) Field of Classification Search
CPC .......................... G06F 19/3462; G07F 17/0092
USPC ................................................ 700/233, 242
See application file for complete search history.

(56) References Cited

U.S. PATENT DOCUMENTS

| | | | | |
|---|---|---|---|---|
| 5,852,911 A | * | 12/1998 | Yuyama et al. | ........... 53/168 |
| 6,219,587 B1 | * | 4/2001 | Ahlin et al. | ........... 700/233 |
| 6,714,838 B2 | * | 3/2004 | Scrymgeour et al. | ...... 700/242 |
| 8,215,540 B2 | * | 7/2012 | Szesko et al. | ........... 235/375 |
| 8,958,112 B2 | * | 2/2015 | Matsui et al. | ........... 358/1.16 |
| 2008/0104830 A1 | | 5/2008 | Yuyama et al. | |
| 2013/0018503 A1 | * | 1/2013 | Carson et al. | ........... 700/216 |

FOREIGN PATENT DOCUMENTS

| | | |
|---|---|---|
| JP | 02-028406 | 1/1990 |
| JP | 02-219705 | 9/1990 |

(Continued)

OTHER PUBLICATIONS

International Search Report, Application No. PCT/JP2011/059215 dated Jun. 7, 2011, 2 pages.

*Primary Examiner* — Patrick Cicchino
(74) *Attorney, Agent, or Firm* — Rankin, Hill & Clark LLP

(57) ABSTRACT

An information display integrating a display portion, a built-in electronic circuit, and a wireless receiver is attached to a container. Medicine dispensers are provided face a conveying path of a container conveying mechanism. The medicine dispensers put a medicine into the container when the medicine is in stock, and issues information on stockout medicine rather than dispensing a medicine when the medicine is out of stock. A write command is wirelessly transmitted to the information display so as to cause the stockout information to be displayed on the display portion in a visibly recognizable manner. In addition, partition information on the planar arrangement of sub containers that allows partitioning the internal space of the container is displayed on the display portion in a visually recognizable manner.

16 Claims, 14 Drawing Sheets

(56) References Cited

FOREIGN PATENT DOCUMENTS

| JP | 11-226089 | 8/1999 |
| JP | 2002-153542 | 5/2002 |
| JP | 2004-148034 | 5/2004 |
| JP | 2005-040371 | 2/2005 |
| JP | 2006-150036 | 6/2006 |
| JP | 2006-239046 | 9/2006 |
| JP | 2009-026329 | 2/2009 |
| JP | 2011-083406 | 4/2011 |

* cited by examiner

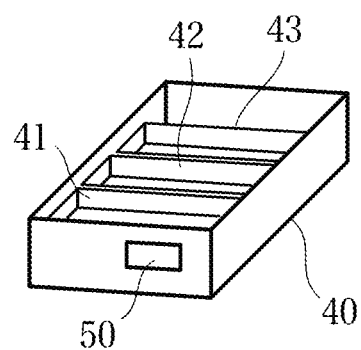

MEDICINE DISPENSING SYSTEM

TECHNICAL FIELD

The present invention relates to a medicine dispensing system operable to keep various sorts of medicines such as injections in stock and to automatically put a medicine indicated in prescription data or pharmaceutical indication data derived from the prescription data into a container so as to dispense the medicine, and more particularly to a medicine dispensing system including an information display for displaying visibly recognizable and rewritable information attached to a container and/or a medicine transporting vehicle to allow the information displayed on the information display of the container to be read visually or mechanically to utilize the information for identification of the container.

BACKGROUND ART

A medicine dispensing apparatus operable to handle medicines in press through package (PTP), a medicine wrapping device operable to handle discrete medicines, and an automatic injection ampule feeding apparatus operable to handle injection medicines have been put into practical use as an automated medicine dispenser for medicines such as tablets and capsules. Further, a medicine dispensing system in which the medicine dispenser described above is provided to face a container (tray) conveying mechanism and a dispensing target medicine is put from the dispenser into a container being conveyed so that an indicated medicine is collected in the container to be dispensed has also been put into practical use (see Japanese Patent Application Publication No. 2002-153542, for example). In the medicine dispensing system, the container is provided with a label into which container (tray) identification information in the form of a barcode, for example, can be written. In the medicine dispensing system, visibly recognizable information can be can be rewritten into the label in a non-contact manner using laser light.

Meanwhile, an electronic stock tag integrating electronic paper serving as an information display having advantages of both electronic data and printed matter, a built-in electronic circuit operable to control drive and store data related to display on the electronic paper, and a wireless receiver operable to receive such data and a command such as a display information rewriting command has been put into practical use (see Japanese Patent Application Publication No. 2009-026329, for example). In an electronic stock tag system provided with a large number of electronic stock tags, the electronic stock tags can be accessed using a transceiver (wireless transmitter) fixedly installed and connected to a server (wireless control unit) via a LAN, and information displayed on the electronic stock tags can be changed using a portable remote controller (wireless controller).

[Patent Document 1] Japanese Patent Application Publication No. 2002-153542

[Patent Document 2] Japanese Patent Application Publication No. 2009-026329

SUMMARY OF INVENTION

Technical Problem

The medicine dispensing system according to the related art discussed above uses a thermal label as the label on the container. Therefore, the label may be adequately written only when the label is stationary whether the label is written in a contact manner or in a non-contact manner. Thus, the label is written while conveyance of the container is stopped. This reduces the throughput (efficiency) by an amount corresponding to the time of the stoppage of the conveyance. In order to minimize such a reduction in efficiency, the number of times that the label is written is suppressed to a minimum. For example, the label is written only when an empty container is fed.

The electronic stock tags and the electronic stock tag systems discussed above have become steadily available at inexpensive prices. Thus, it is conceivable that the medicine dispensing system may switch to the use of the electronic stock tag discussed above in place of the label attached to the container so that the label on the container is a label device capable of wireless reception, enhancing the degree of freedom and the flexibility in rewriting the label.

However, such an advantage is not enough to compensate for the cost incurred to introduce wireless equipment. Thus, it is requested to enhance the processing capacity to a satisfactory level in terms of cost performance.

A technical issue to be addressed is to further improve a medicine dispensing system in order not only to allow a label to be more freely rewritten but also to drastically improve the efficiency by introducing a label device capable of wireless reception.

Solution to Problem

In the following description of the present invention, the term "container" means a container configured to contain medicines and transportable by a conveying mechanism or by hand. Examples of the container include a shallow tray and a rectangular box.

The term "information display" refers to an information display member having a communication function and including a display portion for displaying rewritable information in a visibly recognizable manner. The information display member may be attached, e.g. affixed, to a surface of the container, and may be removable as long as the information display member is attached to the container and/or a medicine transporting vehicle during use of the container.

Further, the term "medicine transporting vehicle" refers to both a handcart having no power source and a conveying vehicle having a power source.

The medicine dispensing system according to a first aspect of the present invention has been devised to address the foregoing issue, and includes a container provided with an information display having a communication function and including a display portion for displaying rewritable information in a visibly recognizable manner, a container conveying mechanism operable to convey the container, a medicine dispenser provided to face a conveying path of the container conveying mechanism, and a dispensation control device. The dispensation control device transmits display information to the information display based on pharmaceutical indication data so as to cause the information to be displayed on the display portion, and outputs to the container conveying mechanism and the medicine dispenser a command for controlling cooperation between the container conveying mechanism and the medicine dispenser so as to cause one or more sorts of indicated medicines to be dispensed from the medicine dispenser to the container. The medicine dispenser is configured to notify the dispensation control device of information on stockout medicine if any. The dispensation control device is configured to transmit a write command to the information display upon receipt of the information on stockout medicine from the medicine dispenser so as to cause the information on stockout medicine to be displayed on the display portion in a visibly recognizable manner.

The stockout information may be text information that describes a stockout status. In this case, the stockout information preferably indicates the name and the quantity of a stockout medicine.

In the medicine dispensing system according to the first aspect of the present invention, if there is no stockout medicine, the medicine dispenser puts a medicine into a container to continue automatic dispensation as in the related art. If there is a stockout medicine, however, notification of information on stockout medicine is issued to continue automatic dispensation without interruption by avoiding input of a medicine and waiting for replenishment, rather than automatic dispensation is temporarily stopped to be resumed after replenishment of the stockout medicine as in the related art. Because automatic dispensation is continued irrespective of the presence or absence of a stockout medicine, not only a process related to the container with a stockout medicine but also processes related to a large number of following containers are smoothly and immediately performed without a hitch. Thus, the efficiency is advantageously significantly improved by the continuance of automatic dispensation. The container with a stockout medicine is subsequently replenished with the stockout medicine. Because the information on stockout medicine is displayed on the display portion in a visibly recognizable manner, replenishment of a stockout medicine can be easily performed even by hand. Thus, according to the present invention, the efficiency can be drastically improved.

Preferably, the dispensation control device further includes matching data storing means, computing means, and display instructing means. The matching data storing means stores medicine-sub container matching data on matching between a plurality of sorts of medicines and sub containers capable of containing such medicines. The computing means determines planar arrangement of the sub containers in the container with reference to the medicine—sub container matching data to dispose in an internal space of the container the one or more sub containers containing the one or more sorts of medicines indicated by the pharmaceutical indication data and to partition the internal space of the container. The display instructing means transmits partition information on the planar arrangement determined by the computing means to the information display so as to cause the determined planar arrangement to be displayed on the display portion. This configuration allows an operator to easily and immediately straighten the medicines by seeing the partition information when he/she divides the internal space of the container using the planar arrangement of several sub containers to straighten the medicines. Thus, according to the present invention, the efficiency can be drastically improved.

Further, the partition information may be displayed in a field for the stockout information by overwriting the stockout information with the partition information. This allows both the partition information and the stockout information to be displayed without excessively expanding the display surface.

The medicine dispensing system according to a second aspect of the present invention, which can be combined with the medicine dispensing system according to the first aspect, includes a medicine dispenser operable to contain a medicine and feed the medicine to a plurality of containers, a medicine transporting vehicle capable of conveying the plurality of containers and provided with an information display having a communication function and including a display portion for displaying rewritable information in a visibly recognizable manner, a container loading device operable to load the plurality of containers onto the medicine transporting vehicle, and a dispensation control device. The dispensation control device gives a load command to the container loading device based on information indicating a medicine transporting destination, and transmits display information to the information display so as to cause at least information on the medicine transporting destination and whether or not a following medicine transporting vehicle is present to be displayed on the display portion of the information display. In the medicine dispensing system according to the second aspect, the medicines dispensed to be contained in the containers are loaded onto the medicine transporting vehicle as grouped according to transporting destinations such as wards, and not only the transporting destination but also information on the vehicle is displayed on the display portion of the information display of the medicine transporting vehicle. Moreover, the displayed information on the vehicle includes the loading order of medicine transporting vehicles for the same medicine transporting destination and whether or not a following medicine transporting vehicle is present. Therefore, it is possible to immediately know whether or not there is any other medicine transporting vehicle that can be moved together to improve the operating efficiency, and if any, what is a preferable order, by seeing any of the medicine transporting vehicles. Thus, according to the present invention, it is possible to realize a medicine dispensing system in which the medicine transporting vehicle can display in a visibly recognizable manner not only a medicine transporting destination but also other useful information.

The dispensation control device generates the load command based on information identifying the medicine transporting destination such that the containers for the same medicine transporting destination are not mixedly loaded with the containers for a different destination, and such that the containers for the same medicine transporting destination are loaded onto one medicine transporting vehicle if the one medicine transporting vehicle can accommodate all of such containers, and otherwise onto a plurality of medicine transporting vehicles. Preferably, if a plurality of containers for the same medicine transporting destination are loaded distributedly onto a plurality of medicine transporting vehicles, the dispensation control device determines, based on prescription information or other information identifying a subject patient, whether or not a plurality of the containers containing medicines to be prescribed for the same patient are loaded distributedly onto a plurality of the medicine transporting vehicles, and causes the information displays of the medicine transporting vehicles for respective medicine transporting destinations to display distribution information indicating the patient relevant to the distributed loading and a distribution status of the distributedly loaded containers. With this configuration, when distributed loading is performed for a patient, the patient relevant to the distributed loading and the distribution status of the distributedly loaded containers are displayed. Thus, it is possible to immediately know that distributed loading has been performed, and to regroup the distributedly loaded containers according to patients with ease and accuracy, by seeing the information display to confirm the transporting destination etc.

BRIEF DESCRIPTION OF DRAWINGS

FIG. 5 is a perspective view showing the appearance of the container, the internal space of which is partitioned by sub containers.

DESCRIPTION OF EMBODIMENTS

A medicine dispensing system according to an embodiment of the present invention will be described with reference to the drawings.

Figure 1:
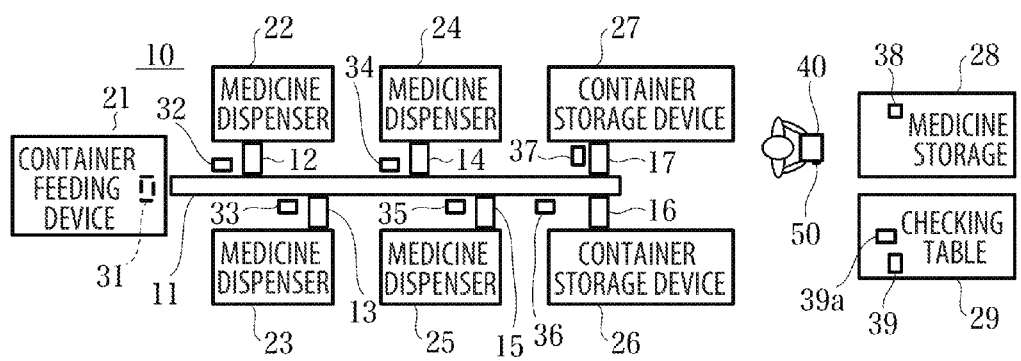
FIG. 1 shows the planar arrangement of the entire medicine dispensing system according to a first embodiment of the present invention.

A medicine dispensing system 10 according to the embodiment of the present invention shown in FIG. 1 includes a plurality of containers 40 each provided with a label device, that is, an information display 50, for a medicine to be automatically collected and dispensed to the container 40, a container conveying mechanism 11 operable to convey the plurality of containers 40 in one direction, for example, a container feeding device 21 provided to face the start point, that is, the most upstream position, of the container conveying path of the container conveying mechanism 11, several medicine dispensers 22 to 25 provided to face the container conveying path of the container conveying mechanism 11 between the start and end points of the conveying path, and container storage devices 26 and 27 provided to face the end point, that is, the most downstream position, of the container conveying path of the container conveying mechanism 11.

A medicine storage 28 for manual replenishment of the containers 40 with a complementary medicine and a checking table 29 for performing a dispensation check by visually confirming whether or not the medicines collected and dispensed to the container 40 are appropriate are provided at a location slightly away from the container conveying path.

Further, container drawing devices 12 to 15 are provided between the container conveying mechanism 11 and the medicine dispensers 22 to 25, respectively, and container drawing devices 16 and 17 are provided between the container conveying mechanism 11 and the container storage devices 26 and 27, respectively. The container drawing devices 12 to 17 each temporarily draws the target container 40 from the container conveying path of the container conveying mechanism 11 to cause the target container 40 to be temporarily stopped in front of the corresponding processing device (22 to 27) without blocking the container conveying path. The container drawing devices 12 to 15 and 16 and 17 correspond to the medicine dispensers 22 to 25 and the container storage devices 26 and 27, respectively.

Figure 2:
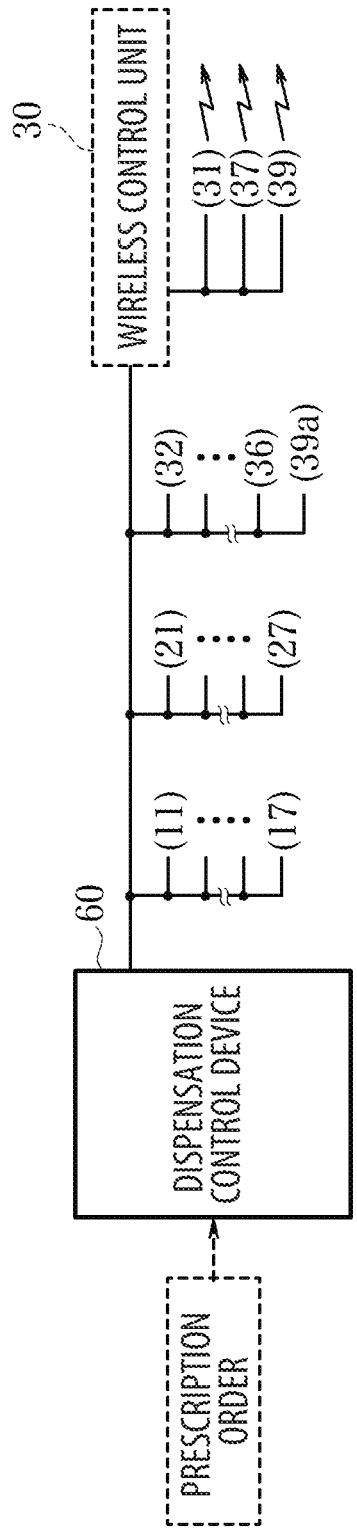
FIG. 2 is a schematic block diagram of a control system.

In addition, a wireless transmitter 31 is provided in the vicinity of a container exit of the container feeding device 21. Identification information reading devices 32 to 36 are provided at the slightly upstream side of the container drawing devices 12 to 16, respectively. A wireless transmitter 37 is provided in the vicinity of the container drawing device 17. A wireless controller 38 is placed at the medicine storage 28. A wireless transmitter 39 and an identification information reading device 39a are provided at the checking table 29. Further, as shown in FIG. 2, a dispensation control device 60 is provided to control operation of the plurality of devices (11 to 39a) discussed above so as to cause the devices to cooperate with each other. The dispensation control device 60 and the devices 11 to 39a can send and/or receive a command, data, or a signal via an appropriate LAN cable or signal cable. A wireless control unit 30 may be interposed between the wireless transmitters 31, 37, and 39 and the dispensation control device 60. However, no wireless control unit 30 may be provided as long as wireless control is possible in the wireless transmitters and the dispensation control device. The dispensation control device 60 receives a prescription order including pharmaceutical indication data from an upper-level controller.

Each device and unit described above may be embodied by using or partially modifying the existing product, and thus will be not be described in detail but described only briefly (see Japanese Patent Application Publication No. 2002-153542, for example).

The container conveying mechanism 11 may be of a belt conveyor type in many cases, but may be of other types such as a rail type. The container drawing devices 12 to 17 may conveniently be structured to push and pull a container using an arm, but may be structured to include a belt conveyor with a direction changing function.

The container feeding device 21 keeps a large number of empty containers 40 in stock, and takes out the containers 40, one at a time, to feed the container 40 onto the container conveying path of the container conveying mechanism 11.

The medicine dispensers 22 to 25 are each an automated medicine dispensing apparatus known in the art configured to keep various sorts of medicines in stock and to put the medicine to be dispensed into the container 40 on the container drawing devices 12 to 15. Examples of such an automated medicine dispensing apparatus include an automatic injection ampule feeding apparatus operable to handle injection medicines (see Japanese Patent Application Publication No. Hei 02-28406), a medicine dispensing apparatus operable to handle medicines in press through package (PTP) (see Japanese Patent Application Publication No. Hei 02-219705), a medicine packaging device operable to handle discrete medicines (see Japanese Patent Application Publication No. Hei 11-226089), and a medicine dispensing apparatus operable to handle transfusions and adjuvants. It should be noted, however, that the medicine dispensers 22 to 25 used in the embodiment have been improved so as to notify the dispensation control device 60 of stockout information on medicine such as the medicine code and the quantity of a stockout medicine if any, that is, when a medicine handled by the medicine dispensers 22 to 25 is to be dispensed even if the medicine is out of stock, unlike the medicine dispensers according to the related art which stop dispensing operation to wait until replenishment of the stockout medicine.

The container storage devices 26 and 27 each receive the containers 40 containing medicines, one at a time, byway of the container drawing devices 16 and 17, respectively, to temporarily store the containers 40 in such a manner that the containers 40 can be taken out by hand. The container storage devices 26 and 27 are selectively used depending on the presence or absence of a stockout medicine. The container storage device 26 stores the containers 40 with no stockout medicine. The container storage device 27 stores containers 40 with a stockout medicine.

Figure 3:
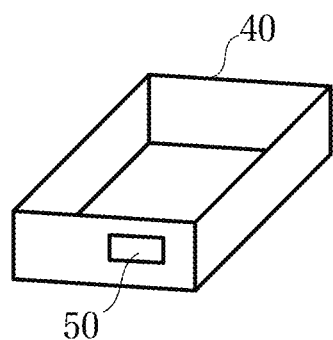
FIG. 3 is a perspective view showing the appearance of a container.

As shown in FIG. 3, the container 40 is a rectangular box opening upward in many cases. As a matter of course, however, the container 40 may be shaped differently as long as the container 40 can contain medicines in the internal space thereof to transport the medicines. An information display having a communication function and including a display portion for displaying information in a visibly recognizable manner is attached to an outer surface of the container 40 in place of a label according to the related art. In the embodiment, an electronic stock tag known in the art, for example, may be used as the information display.

Figure 4:
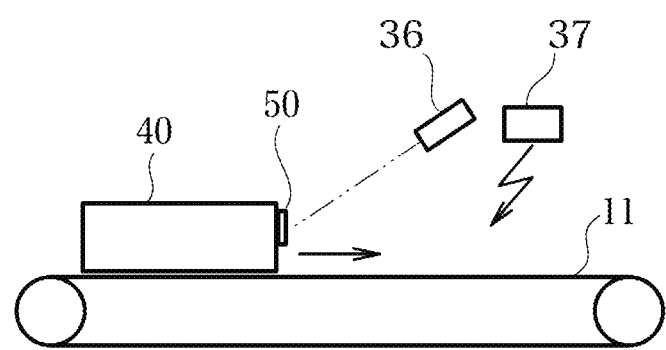
FIG. 4 is a side view of a container conveying mechanism.

As shown in FIG. 4, when the container conveying mechanism 11 conveys the container 40, the container 40 is conveyed with the surface of the container 40 provided with the information display 50 facing forward in the moving direction of the container 40. If the identification information is in the form of a barcode, for example, a laser light scanning barcode reader may be used as the identification information reading devices 32 to 36 disposed for the information display 50. The identification information reading devices 32 to 36 read the identification information displayed on the information display 50 in a non-contact manner from obliquely above and forward of the container 40 during conveyance of the container 40. The identification information reading device 39a on the checking table 29 can read the identification information while the information display 50 is stationary, and thus may be of a contact type. As a matter of course, the identification information reading device 39a on the checking table 29 may also be a non-contact type as with the identification information reading device 32 etc.

In the medicine dispensing system 10, as shown in FIG. 5, sub containers 41 to 43 are used along with the container 40 to straighten the medicines when or after the medicines are dispensed to the container 40. The sub containers 41 to 43 are each a container opening upward and capable of containing medicines put into the container 40 from the medicine dispensers 22 to 25. The sub containers 41 to 43 are each smaller than the container 40. Thus, a plurality of sub containers 41 to 43 can be arranged in the internal space of the container 40. The sub containers 41 to 43 may divide the internal space of the container 40 to partition the internal space. The internal shape of the sub containers 41 to 43 may be set to exclusively contain a particular medicine, or may be set to contain several sorts of medicines of similar sizes in an organized manner. The external shape of the sub containers 41 to 43 is set to suitably partition the internal space of the container 40. For example, if the container 40 has a rectangular internal space, the sub containers 41 to 43 may have smaller rectangular shapes. If the container 40 has a circular internal space, the sub containers 41 to 43 may have a fan shape or a combination of triangular and arcuate shapes.

Figure 6A:
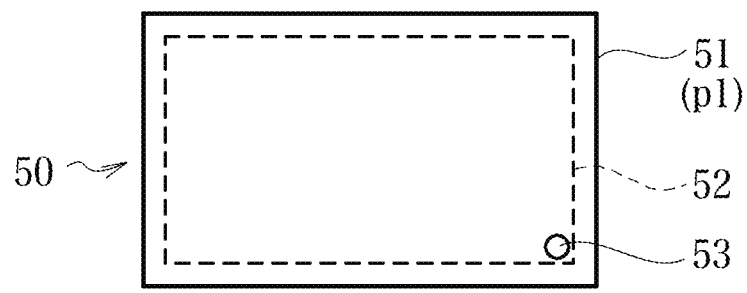
FIGS. 6A and 6B each show an example of a first screen of a label on the container, and FIGS. 6C and 6D each show an example of a second screen of the label on the container.

As shown in FIG. 6A, the information display 50 includes a display portion 51 called electronic paper, a built-in electronic circuit 52, and a wireless receiver 53, which are integrated into a card-shaped housing. However, the information display 50 may be shaped differently as long as the information display 50 can be attached to an outer surface of the container 40, and may have a coin shape, for example. The information display 50 may be attached to the container 40 by any method including bonding, fitting, etc. The basic structure of the information display 50 is the same as that of the electronic stock tag discussed already, and will be described only briefly. The display portion 51, which is electronic paper, is a display medium providing the advantages of a paper display device such as visual recognizability and portability, and the display content of the display portion 51 can be rewritten electrically. Electrophoretic electronic paper and liquid crystal electronic paper, for example, have been put into practical use as the existing electronic paper. The built-in electronic circuit 52 includes one or a plurality of integrated circuits (ICs), and includes a drive circuit for the display portion 51, a memory for storing display data etc., a communication circuit for receiving the display data and a switch display command for switching display, and a programmable control circuit.

The wireless receiver 53 may be a light receiving portion for optical communication that uses infrared radiation, an antenna for radio communication, and a coil or a Hall element for magnetic communication.

In the information display 50 used in the embodiment, the built-in electronic circuit 52 is configured to display a plurality of screens including a first screen p1 and a second screen p2 in order to display much information on the display portion 51 with a limited display area. In the embodiment, when a switch display command is received via the wireless receiver 53, the built-in electronic circuit 52 switches the display content of the display portion 51 to one of the first screen p1 and the second screen p2 according to the received command.

The wireless transmitters 31, 37, and 39 wirelessly access the information display 50. Once the information display 50 as the communication target comes into a communicable range, the wireless transmitters 31, 37, and 39 can transmit write data and a switch display command provided from the dispensation control device 60 to the information display 50 without stopping the container 40 or the information display 50 even during conveyance of the container 40 provided with the information display 50.

The wireless controller 38 shown in FIG. 1 is a so-called remote controller, and wirelessly transmits a command corresponding to an operation performed by an operator to the container 40 by itself. The remote controller used in the embodiment can issue only a switch display command and an erase stockout information command for erasing stockout information, among commands that the dispensation control device 60 transmits to the container 40 via the information display 50.

Figure 7:
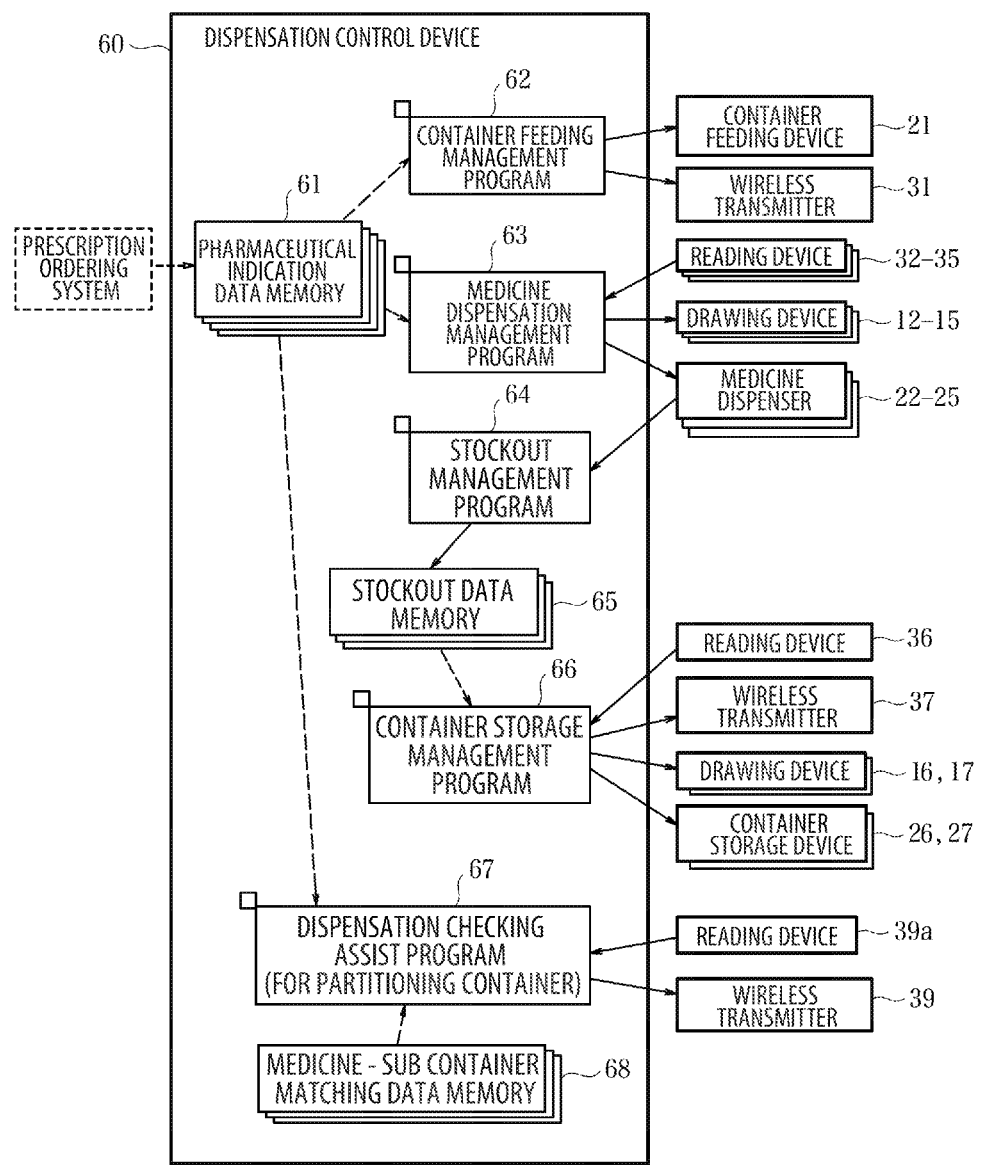
FIG. 7 is a block diagram showing the structure of an example of a dispensation control device.

The dispensation control device 60 shown in FIGS. 2 and 7 is formed to include a programmable computer or sequencer. In the dispensation control device 60, several programs for accessing the container 40 via the wireless transmitters 31, 37, and 39 and the identification information reading devices 32 to 36 and 39a are installed in the programmable computer or sequencer in order not only to control cooperation among the container conveying mechanism 11, the container drawing devices 12 to 17, the container feeding device 21, the medicine dispensers 22 to 25, and the container storage devices 26 and 27 but also to assist manual work performed at the medicine storage 28 and the checking table 29. In addition, a memory in the dispensation control device 60 is assigned to store reference data and update data.

FIG. 7 is a conceptual diagram for illustrating data memories and programs forming the dispensation control device 60 for an occasion where the main component of the dispensation control device 60 is a computer. The dispensation control device 60 accumulates pharmaceutical indication data in a pharmaceutical indication data memory 61. The pharmaceutical indication data are prescription data as they are input from an external prescription ordering system, a dedicated terminal, etc., or include only medicines handled by the medicine dispensers 22 to 25 extracted from the prescription data. Stockout data, which are updated when a medicine becomes out of stock, include the name and the quantity of the stockout medicine, and are accumulated in a stockout data memory 65. The pharmaceutical indication data and the stockout data are correlated with the identification information on the information display 50 of the corresponding container 40 before being stored in the pharmaceutical indication data memory 61 and the stockout data memory 65, respectively. That is, the pharmaceutical indication data for feeding a medicine to a certain container 40 include the identification information (such as ID number) on the container. If a medicine to be fed to a certain container 40 is out of stock, the stockout data include the identification information (such as ID number) on the corresponding container 40. Further, medicine—sub container matching data on matching between a variety of sorts of medicines to be put from the medicine dispensers 22 to 25 into the container 40 and sub containers (41 to 43) capable of containing such medicines are stored in advance in a medicine—sub container matching data memory (matching data storing means) 68. The medicine-sub container matching data are stored in advance in the medicine-sub container matching data memory (matching data storing means) 68 in the form of an indexed table so that data on the sort or the size of a sub container capable of containing a medicine can be obtained when a search is performed using the code of the medicine as a key, for example.

Examples of main programs installed in a memory of a computer (not shown) of the dispensation control device 60 include a container feeding management program 62, a medicine dispensation management program 63, a stockout management program 64, a container storage management program 66, and a dispensation checking assist program 67.

Figure 6B:
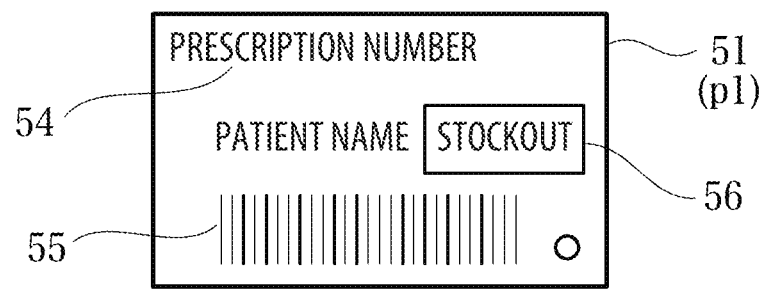

The container feeding management program 62 is a program configured to execute operation for feeding an empty container 40 from the container feeding device 21 to the container conveying mechanism 11, if unprocessed pharmaceutical indication data are stored in the pharmaceutical indication data memory 61, when processing for the unprocessed pharmaceutical indication data is started. The program writes text information 54 such as the prescription number and the patient name, identification information 55 that can be read by the identification information reading devices 32 to 36, and state information 56 such as "UNCHECKED", for example, into the first screen p1 displayed on the display portion 51 of the information display 50 of the container 40 as shown in FIG. 6B, and clears the second screen p2. The identification information 55 includes consecutive numbers displayed in the form of a barcode or the like, and correlates the pharmaceutical indication data for which processing has been started and the container 40 for containing the indicated medicine.

The medicine dispensation management program 63 is a program configured to execute the following operation. First, when the identification information 55 displayed on the information display 50 of the container 40 which has been conveyed to the front of the identification information reading devices 32 to 35 is read by the identification information reading devices 32 to 35 to notify the dispensation control device 60 of the identification information 55, pharmaceutical indication data corresponding to the identification information is referenced to check whether or not the corresponding one of the medicine dispensers 22 to 25 keeps the dispensing target medicine in stock. If the dispensing target medicine is kept in stock, an input medicine command is issued to the corresponding pair of medicine dispenser and container drawing device, among the medicine dispensers 22 to 25 and the container drawing devices 12 to 15.

The stockout management program 64 is a program configured to execute operation for accumulating stockout data in the stockout data memory 65 when the dispensation control device 60 is notified of the stockout information sent from the medicine dispensers 22 to 25.

Figure 6C:
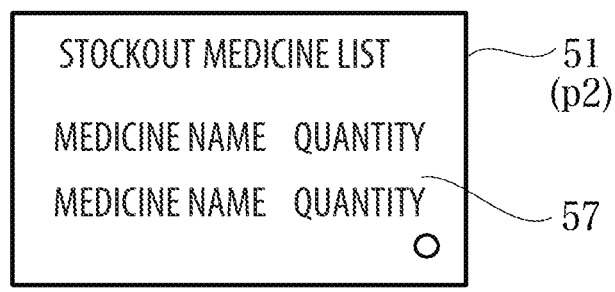

The container storage management program 66 is a program configured to execute the following operation. First, when the identification information 55 displayed on the display portion 51 of the information display 50 of the container 40 which has been conveyed to the front of the identification information reading devices 36 is read by the identification information reading devices 36 to notify the dispensation control device 60 of the identification information 55, it is determined based on the stockout data accumulated in the stockout data memory 65 whether or not there is any stockout medicine for the container 40. If there is no stockout medicine and all the dispensing target medicines are collected in the container 40, a command for containing the container 40 is issued to the container storage devices 26 and the container drawing device 16. If there is a stockout medicine in at least one of the medicine dispensers 22 to 25 and all the dispensing target medicines are not collected in the container 40, however, a command for containing the container 40 is issued to the container storage device 27 and the container drawing device 17, and write data on the stockout information at that time and a write command for causing the stockout information to be displayed on the display portion 51 in a visibly recognizable manner are transmitted to the information display 50 through the wireless transmitter 37. In the example, in which two display screens are provided, only the state information 56 is rewritten as "STOCKOUT", for example, in the first screen p1 (see FIG. 6B), and specific stockout information 57 is additionally written in the second screen p2 (see FIG. 6C).

Figure 6D:
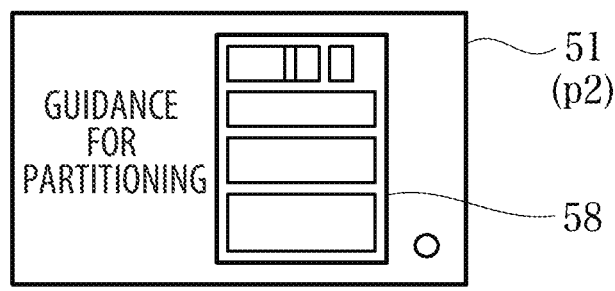

The dispensation checking assist program 67 is a program configured to execute the following operation. First, when the identification information 55 displayed on the information display 50 of the container 40 selected as a dispensation checking target by a dispensation checking person is read by the identification information reading device 39a so that the dispensation control device 60 is notified of the identification information 55, pharmaceutical indication data corresponding to the identification information is displayed on a display (not shown) to assist checking operation. Then, the medicine—sub container matching data memory 68 is referenced to partition the container. Specifically, sub containers that can be used to straighten the medicines already collected in the container 40 are selected from data in the medicine—sub container matching data memory 68. For example, the dispensation checking assist program 67 executes operation for finding planar arrangement of sub containers that allows partitioning the internal space of the container 40 by first arranging the sub containers in the order of size and, when the operation comes to a dead point, postponing the preceding arrangement of sub containers. In addition, write data on partition information obtained through the operation and a write command for causing the information to be displayed on the display portion 51 in a visibly recognizable manner are transmitted to the information display 50 through the wireless transmitter 39. In the embodiment, the partition information 58 is displayed in the field for the stockout information 57 displayed on the second screen p2 in the display portion 51 by overwriting the stockout information 57 with the partition information 58 (see FIG. 6D). As a matter of course, a third screen p3 may be added as a screen to be displayed on the display portion 51 so that the partition information 58 is displayed on the third screen p3 while the stockout information 57 is displayed on the second screen p2. In the embodiment, the dispensation checking assist program 67 is executed by a computer to implement in the dispensation control device 60 computing means for determining planar arrangement of the sub containers in the container with reference to the medicine-sub container matching data to dispose in the internal space of the container one or more sub containers containing one or more sorts of medicines indicated by the pharmaceutical indication data and to partition the internal space of the container, and to implement in the dispensation control device 60 display instructing means for transmitting partition information on the planar arrangement determined by the computing means to the information display 50 so as to cause the determined planar arrangement to be displayed on the display portion 51 of the information display 50.

The mode of use and operation of the medicine dispensing system 10 according to the embodiment will be described with reference to the drawings. FIGS. 8A to 8H each show an example of the first screen p1 or the second screen p2 displayed on the display portion 51 of the information display 50 of the container 40.

When pharmaceutical indication data reach the dispensation control device 60 of the medicine dispensing system 10, the pharmaceutical indication data are input to the dispensation control device 60 to be accumulated in the pharmaceutical indication data memory 61. Thereafter, the dispensation control device 60 automatically controls medicine dispensation based on the pharmaceutical indication data. Along with the control, first, an empty container 40 is fed from the container feeding device 21 onto the container conveying path of the container conveying mechanism 11. Initial display information is written into the information display 50 of the container 40 via the wireless transmitter 31. The write data and the command are wirelessly transmitted from the dispensation control device 60 to the information display 50 during conveyance of the container 40, and thus the data are written into the information display 50 without stopping the conveyance of the container 40.

Figure 8A:
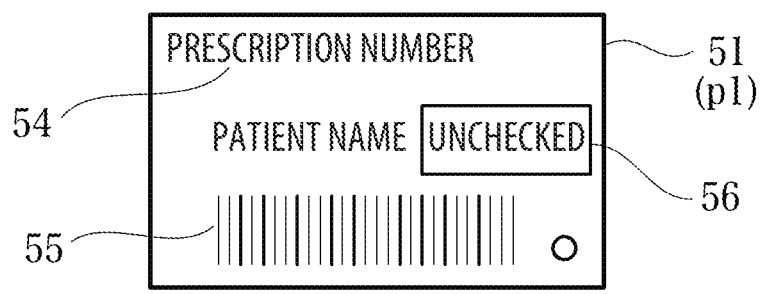
FIGS. 8A to 8H each show an example of the first or second screen of the label on the container.
Figure 8B:
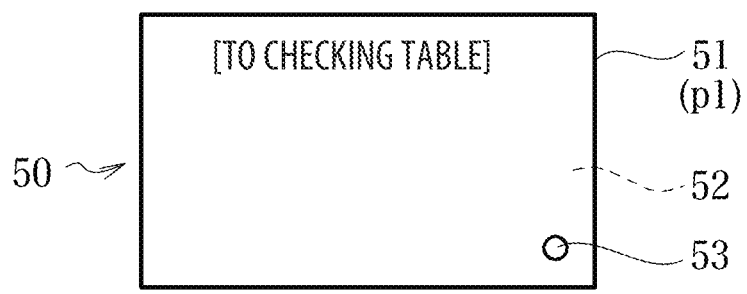

An example of initialization of display information is shown. Based on the pharmaceutical indication data correlated with the container 40 provided with the information display 50 as the writing destination, text information 54 such as the prescription number and the patient name, identification information 55 in the form of a barcode, and state information 56 indicating "UNCHECKED" are written into the first screen p1 of the display portion 51 (see FIG. 8A). Text information indicating the transporting destination after automatic dispensation such as "TO CHECKING TABLE" is written into the second screen p2 of the display portion 51 as shown in FIG. 8B. Information that has been left in the second screen p2 is all erased. During the automatic dispensation since the container 40 is fed from the container feeding device 21 until the container 40 is stored in the container storage devices 26 or 27, the first screen p1 is displayed on the display portion 51 at all times to allow the identification information 55 to be read by the identification information reading devices 32 to 36.

Then, when an empty container 40 is conveyed by the container conveying mechanism 11 and the identification information 55 displayed on the information display 50 is read by the identification information reading device 32 during conveyance, the dispensation control device 60 confirms whether or not there is any medicine to be dispensed from the medicine dispenser 22 to the container 40. If there is no medicine to be dispensed, the container 40 is continuously conveyed to pass by the container drawing device 12. If there is any medicine to be dispensed, the container 40 is drawn by the container drawing device 12 so that the dispensing target medicine is put from the medicine dispenser 22 into the container 40. When the medicine has been put, the container 40 is put back onto the container conveying mechanism 11, which resumes conveying the container 40.

In this event, if the dispensing target medicine is out of stock when the medicine dispenser 22 is to put the medicine into the container 40 to result in a stockout medicine, the medicine is not put in, and instead the dispensation control device 60 is notified of stockout information provided from the medicine dispenser 22, and the information is accumulated in the stockout data memory 65 as stockout data. When the medicine dispenser 22 which issued the stockout information has put medicines that can be dispensed, but not the stockout medicine, into the container 40, the container 40 is put back onto the container conveying mechanism 11.

Although not described in detail to avoid repetition, as the container 40 is conveyed by the container conveying mechanism 11, the same operation as that described above is automatically performed at the identification information reading device 33, the container drawing device 13, and the medicine dispenser 23, at the identification information reading device 34, the container drawing device 14, and the medicine dispenser 24, and at the identification information reading device 35, the container drawing device 15, and the medicine dispenser 25.

When the container 40 which has collected the medicines is conveyed by the container conveying mechanism 11 to the front of the identification information reading device 36, the identification information 55 displayed on the information display 50 is read by the identification information reading device 36 during conveyance of the container 40 to notify the dispensation control device 60 of the identification information 55. The dispensation control device 60 determines based on the stockout data in the stockout data memory 65 whether or not there is any stockout medicine for the container 40. If there is no stockout medicine and all the dispensing target medicines are collected in the container 40, the container 40 is stored in the container storage device 26. If there is a stockout medicine at any of the medicine dispensers 22 to 25 and all the dispensing target medicines are not collected in the container 40, the container 40 is stored in the container storage device 27. Then, stockout information based on the stockout data is written into the information display 50 of the container 40 via the wireless transmitter 37.

Figure 8C:
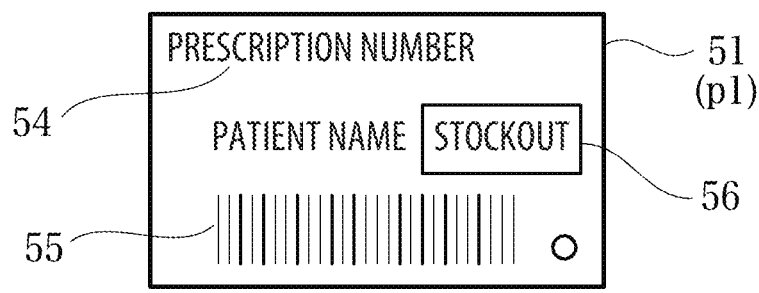
Figure 8D:
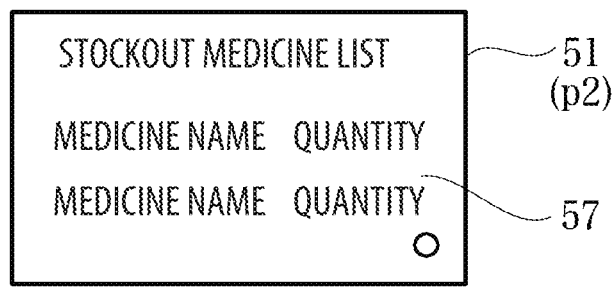

FIG. 8c shows an example of the written stockout information. Text or a symbol indicating the presence of a stockout medicine such as "STOCKOUT" is written into the field for the state information 56 in the first screen p1 of the display portion 51 based on the stockout data correlated with the container 40 provided with the information display 50 as the writing destination. As shown in FIG. 8D, stockout information 57 indicating the name and the quantity of the stockout medicine is written into the second screen p2 of the display portion 51. Also for the stockout information, the write data and the command are wirelessly transmitted from the dispensation control device 60 to the information display 50 during conveyance of the container 40, and thus the data are written into the information display 50 without stopping the conveyance of the container 40.

Then, when such automatic dispensation is repeated, the containers 40 with no stockout medicine are successively stored in the container storage device 26, and the containers 40 with a stockout medicine are stored in the container storage device 27. Since the containers 40 are stored in different storages depending on the presence or absence of a stockout medicine, containers 40 to which a complementary medicine should be added by hand will not be overlooked. The containers 40 lacking a medicine are transferred from the container storage device 27 to the medicine storage 28, where a complementary medicine is additionally put in by hand. At this time, when the operator operates the wireless controller 38 to transmit a switch display command to the information display 50, a stockout medicine list in the second screen p2 is displayed on the display portion 51, facilitating and accelerating putting in a complementary medicine by hand. When the medicine has been put in, the wireless controller 38 is further operated to transmit an erase stockout information command to the information display 50. Then, the display content of the information display 50 becomes the same as that when there is no stockout medicine (see FIG. 8A). When such display is visually confirmed, the operator transfers the container 40 to the checking table 29.

After collecting all the dispensing target medicines in the automatic dispensation, the container 40 is directly transferred from the container storage device 26 to the checking table 29. On the checking table 29, the container 40 is subjected to a dispensation check together with the container 40 transferred from the medicine storage 28. A checking person causes the identification information 55 displayed on the information display 50 of the container 40 as the checking target to be read by the identification information reading device 39a. This allows the dispensation control device 60 to be notified of the identification information, and pharmaceutical indication data corresponding to the identification information are read from the pharmaceutical indication data memory 61, and displayed on a display to assist checking operation. Then, when the dispensation control device 60 is notified by operation input etc. performed by the checking person that the dispensation check has been completed without abnormality, the display information displayed on the information display 50 of the container 40 which has been checked is rewritten via the wireless transmitter 39.

Figure 8E:
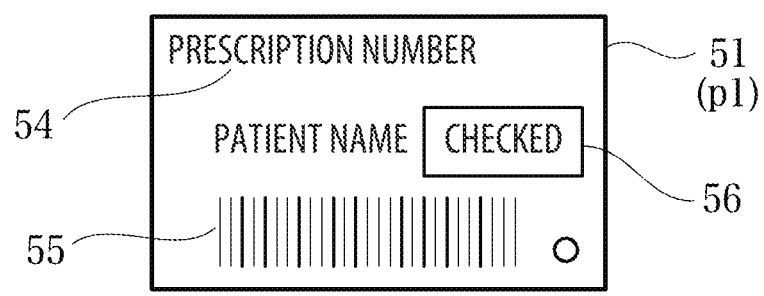
Figure 8F:
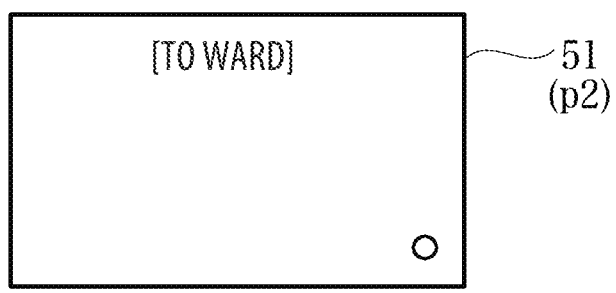

In the embodiment, it can be known whether or not the medicines are straightened utilizing the sub containers by referencing the operation mode set for the dispensation control device 60 and specific parameter values for the pharmaceutical indication data, for example. Further, for the containers 40 in which the medicines are not straightened utilizing the sub containers, text saying "CHECKED" which means that the medicines in the container have been checked is written into the field for the state information 56 in the first screen p1 of the display portion 51 of the information display 50 as shown in FIG. 8E. In addition, text information indicating the transporting destination after a dispensation check such as "TO WARD" is written into the second screen p2 of the display portion 51 as shown in FIG. 8F.

Figure 8G:
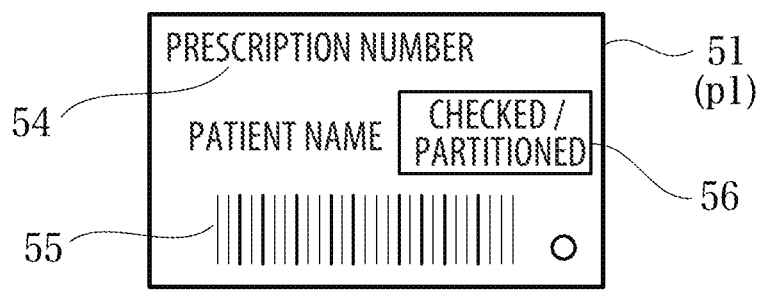
Figure 8H:
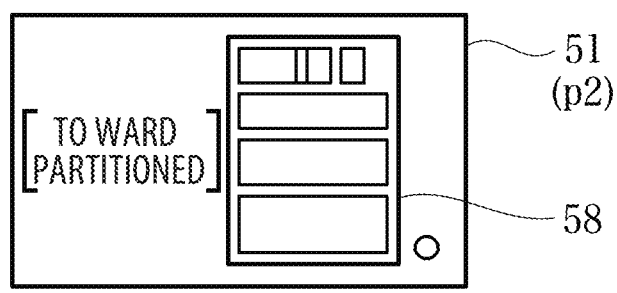

For the containers 40 in which the medicines are straightened utilizing the sub containers, in contrast, the dispensation control device 60 computes to partition the container. After planar arrangement of sub containers that allows partitioning the internal space of the container 40 has been determined through the computation, text saying "CHECKED/PARTITIONED" which means that the medicines in the container have been checked and that guidance for partitioning is provided is written into the field for the state information 56 in the first screen p1 of the display portion 51 of the information display 50 as shown in FIG. 8G. In addition, partition information 58 illustrating the planar arrangement of sub containers is written into the second screen p2 of the display portion 51 as shown in FIG. 8H. The partition information 58 illustrating the planar arrangement of sub containers that allows partitioning the internal space of the container 40 is thus displayed in a visibly recognizable manner. This allows the operator to easily and immediately straighten the medicines by seeing the partition information 58 when he/she divides the internal space of the container 40 using the planar arrangement of several sub containers (components indicated by numerals 41 to 43 in FIG. 5) to straighten the medicines.

If the container 40 lacking a medicine is erroneously discharged without additional input of a complementary medicine, an operator in charge of subsequent transport and organization causes the display portion 51 to display the second screen p2 when he/she would like to see guidance on the transporting destination or guidance on partitioning. Then, a stockout medicine list is displayed to clearly indicate that the content of the container is different from the expected content. This allows the operator to reliably notice the error so that he/she hardly overlooks the error. When the container 40 which has been erroneously forwarded is returned to the medicine storage 28, the stockout medicine list is displayed on the information display 50 of the container 40. Thus, a complementary medicine can be additionally put in to conveniently resume the process.

In the embodiment described above, the container conveying mechanism 11 is linear and configured to convey containers only in one direction. However, the container conveying path may be curved or branched, and may be configured to convey containers in a circulating manner or bi-directionally.

In the embodiment described above, the partition information 58 is written at the checking table 29. However, the partition information 58 may be written at any time before the sub containers 41 to 43 are actually arranged in the internal space of the container 40. Thus, the partition information 58 may be written at a nurse station in a ward, for example.

In the medicine dispensing system according to the embodiment, wireless transmission to the information display 50 is performed during conveyance of the container 40. In this case, information can be written, while the container 40 is being conveyed, by utilizing wireless transmission of display data and a rewrite command to the information display 50, thereby accordingly improving the efficiency. Moreover, information on stockout medicine is also written into the information display 50 in addition to the existing information such as identification information. Because such information is written during conveyance of the container, the improvement in efficiency is not impaired even if the number of times of writing information is increased.

In the medicine dispensing system according to the embodiment described above, the partition information is displayed in a display field for the stockout information in the display portion 51 by overwriting the stockout information with the partition information. Therefore, both the partition information and the information on stockout medicine can be displayed without excessively expanding the display surface. Even if the stockout information is overlooked and a container is sent to be subjected to straightening without replenishment of a complementary medicine, the operator, who attempted to see the partition information, sees the stockout information to notice an error if switching has been performed from display of the partition information to display of the stockout information, enhancing the reliability of medicine dispensation. Therefore, according to the embodiment, an efficient and reliable medicine dispensing system can be achieved.

Figure 9:
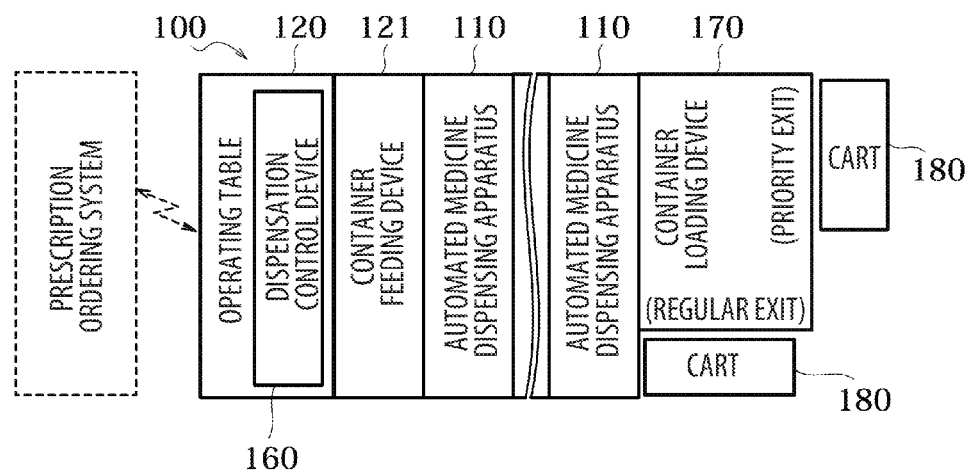
FIG. 9 shows the planar arrangement of a schematic configuration of a medicine dispensing system according to another embodiment.
Figure 10:
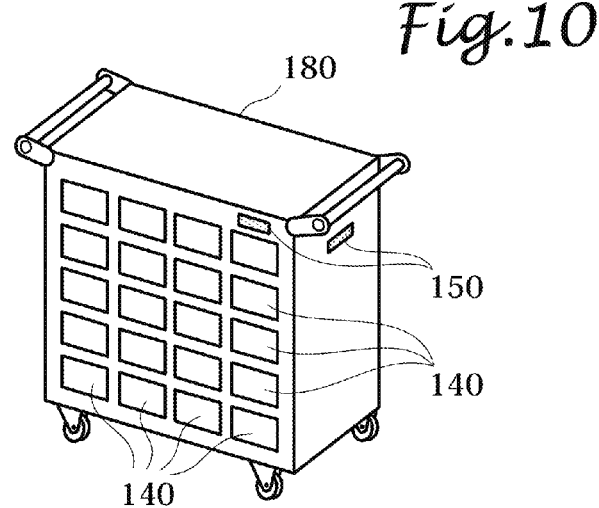
FIG. 10 is a perspective view showing the appearance of a medicine transporting handcart serving as a medicine transporting vehicle loaded with containers.

Next, an example of a medicine dispensing system according to a second aspect of the present invention that can be combined with the embodiment described above will be described with reference to FIGS. 9 to 11. FIG. 9 shows the planar arrangement of a schematic configuration of a medicine dispensing system 100 according to the embodiment. FIG. 10 is a perspective view showing the appearance of a medicine transporting handcart 180 serving as a medicine transporting vehicle loaded with containers 140. FIGS. 11A to 11E each show a display surface of an information display 150.

As shown in FIG. 9, the medicine dispensing system 100 includes an operating table 120 equipped with a dispensation control device 160, and a container feeding device 121, one or more automated medicine dispensing apparatuses 110, a container loading device 170, and one or more medicine transporting handcarts 180, which are arranged along a container conveying path in this order from the upstream side to the downstream side. The automated medicine dispensing apparatuses 110 each have the same configuration as that of the medicine dispensing system 10 shown in FIGS. 1 to 8. In the medicine dispensing system 100, if the one or more automated medicine dispensing apparatuses 110 have a container storage device corresponding to the container storage device 27 shown in FIG. 1, the container loading device 170 is disposed adjacent to the container storage device. If the one or more automated medicine dispensing apparatuses 110 do not have a container storage device corresponding to the container storage device 27 shown in FIG. 1, meanwhile, the container loading device 170 is disposed adjacent to the terminal end portion of the container conveying mechanism 11 shown in FIG. 1. In the following description, it is assumed that the containers 140 lack no medicine and contain all the medicines. In the embodiment, an information display (first information display: see numeral 50 in FIG. 3) attached to the container 140 is not shown. Operation of the automated medicine dispensing apparatus 110 is the same as that in the embodiment shown in FIGS. 1 to 8, and thus will not be described in detail.

The container conveying path may be embedded in the bottom etc. of each device (110, 120, 121, 170), or formed by a container conveying mechanism such as a belt conveyor, for example, provided adjacent to medicine dispensing ports and a container feeding port.

The container feeding device 121 can deliver empty containers 140 to the container conveying mechanism as required, and may store a large number of containers 140 itself (see Japanese Patent Application Publication No. 2002-153542 and Japanese Patent Application No. 2009-238050, for example), or receive containers 140 from another device (see Japanese Patent Application Publication No. 2006-239046, for example).

The automated medicine dispensing apparatus 110 stores a large number of medicines in large amounts in a medicine storage portion etc. and put the medicines into the container 140 according to a control command etc. to feed the medicines, and may put medicines as they are into the container 140 (see Japanese Patent Application Publication No. 2002-153542 and Japanese Patent Application No. 2009-238050, for example), or put medicines which have been put in a bag into the container 140 (see Japanese Patent Application Publication No. 2004-148034, for example).

The container loading device 170 can receive the containers 140 sent from the automated medicine dispensing apparatuses 110 and containing the medicines to load the containers 140 onto the medicine transporting handcart 180, and may have only one container loading exit for the medicine transporting handcart 180 to approach (see the first embodiment and FIG. 1 of Japanese Patent Application Publication No. 2002-153542, for example), or have a plurality of container loading exits (see the second embodiment and FIG. 2 of Japanese Patent Application Publication No. 2002-153542, for example). In the specific example here, the container loading device 170 is provided with two container loading exits, namely a regular exit and a priority exit.

The medicine transporting handcart 180 (see FIG. 10), which is generally referred to as a medicine cart, can be loaded with a plurality of containers 140 and pushed by hand to be transported, and may not be provided with a traveling function etc. (see Japanese Patent Application Publication No. 2005-040371, for example) or not be provided with an information carrier for e.g. container arrangement specifying information (see Japanese Patent Application Publication No. 2006-239046, for example). However, the medicine transporting handcart 180 is provided with at least one information display 150 (second information display) at a visible location such as on an outer surface with its display surface exposed. While the medicine transporting handcart 180 loaded with 20 containers 140 is shown, it is assumed that the medicine transporting handcart 180 can be loaded with up to 27 containers 140 in the following numerical example.

As the information display 150 (see FIG. 10 and FIG. 11A), a card-shaped device similar to the information display 50 discussed earlier integrating a display portion 151 and a built-in electronic circuit and a wireless receiver (not shown) is used (see Japanese Patent Application Publication No. 2009-026329 and Japanese Patent Application No. 2009-238050, for example). The information display 150 is attached, e.g. affixed, at an easily visible location on a surface of the medicine transporting handcart 180, and may be removable as long as the information display 150 is attached during use of the medicine transporting handcart 180.

Further, although not shown, a wireless transmitter configured to wirelessly access the information display 150 is provided as means for rewriting the display content of the information display 150. The wireless transmitter is provided to the container loading device 170 or the automated medicine dispensing apparatus 110 close to the container loading device 170, or attached to a dedicated table or support post, so that write data and a switch display command provided from the dispensation control device 160 can be transmitted to the information display 150 of the medicine transporting handcart 180 at the regular exit or the priority exit of the container loading device 170. A plurality of wireless transmitters may be provided to be selectively used for the regular exit and the priority exit, for example, or a wireless transmitter may be used commonly by identifying the medicine transporting handcart using a cart number etc.

The dispensation control device 160 is a programmable information processing device such as a personal computer or a microprocessor system, and formed inside the operating table 120 to acquire prescription information by receiving an operation performed using the operating table 120, downloading from an external prescription ordering system, or the like.

The prescription information may be prescription data as they are, or may be pharmaceutical indication data obtained by extracting a portion of the prescription data required for medicine dispensation or processing the prescription data to be suitable for medicine dispensation. The prescription information includes information required for medicine dispensation such as the sort and the quantity of a medicine. In many cases, the prescription information additionally includes information identifying a subject patient such as the name and the sex of a patient to which the dispensed medicine is to be administered, and information identifying a medicine transporting destination such as a ward or an operating room in which the dispensed medicine is to be used. However, one or both of the two pieces of information may not be included.

For example, if the prescription information is used to prepare in advance a set of medicines determined in advance according to an operative procedure before the location and the subject patient of the operation are decided, information identifying the subject patient or the medicine transporting destination may not be included in the prescription information yet at the time of medicine dispensation.

The dispensation control device 160 is connected to the container feeding device 121, the automated medicine dispensing apparatuses 110, and the container loading device 170 via an appropriate signal cable, LAN cable, or the like to transmit an operation command to and receive the device state from the devices in order to cause the devices to cooperate with each other based on the acquired prescription information. The dispensation control device 160 can wirelessly access the information display 150 of the medicine transporting handcart 180 located at the regular exit or the priority exit of the container loading device 170 via a wireless transmitter to rewrite the display content of the information display 150. Each time prescription information is acquired, the dispensation control device 160 causes the container feeding device 121 to sequentially feed empty containers 140 to the automated medicine dispensing apparatus 110. The dispensation control device 160 causes the automated medicine dispensing apparatuses 110 to put prescribed medicines into the container 140, and to deliver the container 140 into which the medicines have been put to the container loading device 170.

Further, the dispensation control device 160 causes the container loading device 170 to load the container 140 onto the medicine transporting handcart 180 at the regular exit or the priority exit. If a medicine transporting destination is identified from the corresponding prescription information when the container loading device 170 is caused to load the container 140 onto the medicine transporting handcart 180, the dispensation control device 160 uses the medicine transporting destination. If a medicine transporting destination is not identified from the prescription information, however, the dispensation control device 160 uses the medicine transporting destination input from the operating table 120 etc. if specified so by the operation mode. The dispensation control device 160 determines, as much as possible, the medicine transporting destination of the container 140 that is about to be loaded, and if the medicine transporting handcart 180 at the regular exit is empty, decides that the medicine transporting destination of the container 140 that is about to be loaded is the medicine transporting destination of the medicine transporting handcart 180 at the medicine transporting destination. The dispensation control device 160 causes the medicine transporting destination to be displayed in the field for a transporting destination indication 154 of the information display 150 of the medicine transporting handcart 180, and further causes the container loading device 170 to load the container 140 onto the medicine transporting handcart 180 at the regular exit.

If the medicine transporting handcart 180 at the regular exit is not empty and the medicine transporting destination has already been decided, in contrast, the dispensation control device 160 compares the medicine transporting destination of the container 140 that is about to be loaded and the medicine transporting destination of the medicine transporting handcart 180 at the regular exit. If the medicine transporting destinations match each other, the dispensation control device 160 controls the container loading device 170 to load the container 140 onto the medicine transporting handcart 180 at the regular exit. If the medicine transporting destinations do not match each other, or if the medicine transporting destination cannot be determined, the dispensation control device 160 controls the container loading device 170 to load the container 140 onto the medicine transporting handcart 180 at the priority exit. If the medicine transporting handcart 180 is fully loaded with the containers 140, the dispensation control device 160 prompts the operator through display on the operating table 120 to replace the medicine transporting handcart 180 with an empty medicine transporting handcart 180, and postpones loading the next container 140 until an empty medicine transporting handcart 180 arrives.

Because of such control performed by the dispensation control device 160, the medicine dispensing system 100 enables the containers 140 for the same medicine transporting destination not to be mixedly loaded with the containers for a different destination, and enables the containers 140 for the same medicine transporting destination to be loaded onto one medicine transporting vehicle 180 if the one medicine transporting vehicle 180 can accommodate all of such containers 140, and otherwise onto a plurality of medicine transporting vehicles 180. The medicine transporting destination is displayed in the field for the transporting destination indication 154 of the information display 150 provided to the medicine transporting handcart 180 as the loading destination (see FIG. 11).

Further, as shown in FIG. 11, the dispensation control device 160 causes handcart information to be displayed in the field for a handcart information indication 155 of the information display 150. The handcart information indicates the loading order of the medicine transporting handcarts 180 for the same medicine transporting destination, and whether or not a following medicine transporting handcart is present. A typical example of indication of the loading order includes integers starting from 1. Here, the loading order indicates the order in which a plurality of medicine transporting handcarts 180 for the same medicine transporting destination are loaded. Indication of whether or not a following medicine transporting handcart is present may be text saying "FOLLOWING HANDCART PRESENT" or "NO FOLLOWING HANDCART". Here, however, the loading order of the next medicine transporting handcart 180 is used as indication of whether or not a following medicine transporting handcart is present if there is such a following medicine transporting handcart. Otherwise, the loading order of the current medicine transporting handcart 180 is used as indication of whether or not a following medicine transporting handcart is present. Indication "CART 1/2" provided in the field for the handcart information indication 155 shown in FIG. 11B indicates that the medicine transporting handcart 180 is the first cart to be loaded, and that there is a second cart to be loaded. Thus, in the embodiment, whether or not a following medicine transporting handcart is present is indicated by whether or not the two numbers before and after a slash (/) match each other. In addition, the number of containers 140 actually loaded onto the medicine transporting handcart 180 and the maximum number of containers 140 that can be loaded onto the medicine transporting handcart 180 are also displayed in the field for the container information indication 156 of the information display 150. In FIG. 11A, the number "10/27" is shown, and indicates that 10 containers 140 have been loaded and that up to 27 containers 140 can be loaded.

When loading the containers 140 onto the medicine transporting handcarts 180, if the containers 140 for the same medicine transporting destination are loaded distributedly onto a plurality of medicine transporting handcarts 180, the dispensation control device 160 determines, based on prescription information or other information identifying a subject patient, whether or not a plurality of containers 140 containing medicines to be prescribed for the same patient are loaded distributedly onto a plurality of medicine transporting handcarts 180. If the dispensation control device 160 determines that the containers are distributedly loaded, distribution information indicating the patient relevant to the distributed loading such as the patient name, for example, and the distribution status of the distributedly loaded containers such as the numerator (a serial number of each distributedly loaded container) and the total number, for example, is displayed in the field for a distribution information indication 157 of the information displays 150 provided to the medicine transporting handcarts 180 for respective medicine transporting destinations.

Figure 11A:
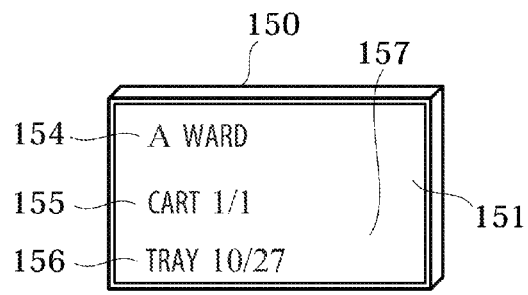
FIGS. 11A to 11E each show a display surface of an information display.
Figure 11B:
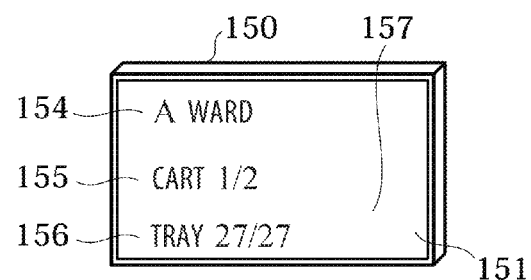
Figure 11C:
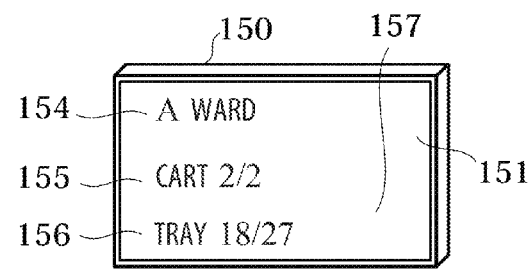
Figure 11D:
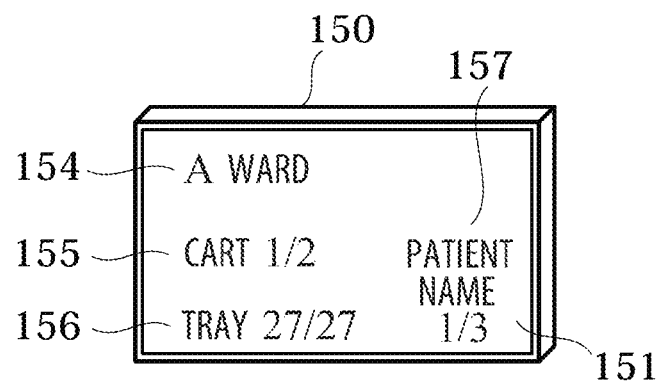
Figure 11E:
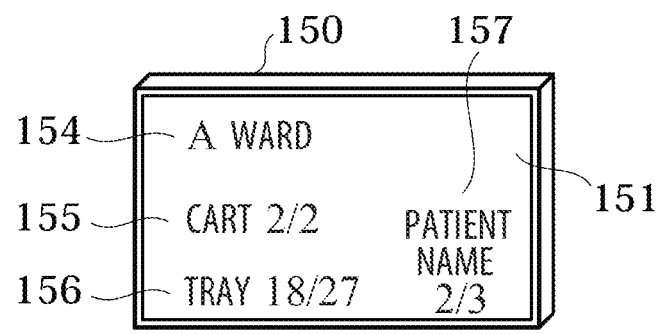

The mode of use and operation of the medicine dispensing system 100 according to the second embodiment will be described with reference to the drawings. FIG. 11A shows a display example for an occasion where one medicine transporting handcart 180 can accommodate all the medicines to be transported to an A ward. FIGS. 11B and 11C each show a display example for an occasion where two medicine transporting handcarts 180 are required to accommodate all the medicines to be transported to the A ward. FIGS. 11D and 11E each show a display example for an occasion where three containers 140 containing the medicines for one patient are distributedly loaded onto two medicine transporting handcarts 180.

The operating table 120 (dispensation control device 160), the container feeding device 121, the automated medicine dispensing apparatuses 110, and the container loading device 170 of the medicine dispensing system 100 are coupled through a signal cable or a container conveying mechanism, and fixedly installed in a medicine dispensing department of a hospital, an on-site pharmacy, or the like. The medicine transporting handcarts 180 of the medicine dispensing system 100 are to be loaded with the containers 140 containing medicines to transport the containers 140. Thus, the medicine transporting handcarts 180 are pushed by hand to be moved between a medicine dispensing department etc. where the container loading device 170 is installed and a ward where the medicines are to be used. The transporting destination indication 154 on the information display 150 attached to the medicine transporting handcart 180 is rewritten when the containers 140 are loaded onto the medicine transporting handcart 180. Thus, the medicine transporting handcarts 180 can be used for conveyance to any medicine transporting destination, rather than being exclusively used for conveyance to one medicine transporting destination, if there are a plurality of medicine transporting destinations.

That is, all the containers 140 are taken out of the medicine transporting handcart 180 having returned to the medicine dispensing location, irrespective of where it has returned from, and the medicine transporting handcart 180 is placed at any empty regular exit or priority exit of the container loading device 170. Then, pieces of prescription information are sent one after another from the prescription ordering system, and additional pieces of prescription information are further input from the operating table 120 (dispensation control device 160), so that prescription information to be processed by the medicine dispensing system 100 is accumulated in the control device of the operating table 120. When the accumulated prescription information amounts to one prescription unit or more, the prescription information is sequentially processed by the dispensation control device 160, irrespective of whether or not any further prescription information is present. Then, under control by the dispensation control device 160, an empty container 140 is fed from the container feeding device 121, and prescribed medicines are put into the container 140 from one or more automated medicine dispensing apparatuses 110. A plurality of containers 140 containing medicines are loaded onto a medicine transporting handcart 180 by the container loading device 170.

Many pieces of prescription information accumulated in the dispensation control device 160 have a determined medicine transporting destination, and are at a regular level, which means that such pieces of prescription information can be regularly processed according to schedules. However, other pieces of prescription information may be at an emergent level, which means that such pieces of prescription information must be preferentially processed as an interrupt, or at an extraordinary level which falls between the regular level and the emergent level, or may not have a determined medicine transporting destination. Schedules are determined such that pieces of prescription information at the regular level for the same medicine transporting destination are collectively processed as much as possible. However, prescription information at the emergent level or the extraordinary level may be processed as an interrupt in the middle of a series of processes for prescription information at the regular level. Thus, in order to both prevent mixed loading and improve the efficiency, the containers 140 corresponding to prescription information at the regular level are loaded onto the medicine transporting handcart 180 at the regular exit. Meanwhile, the containers 140 corresponding to prescription information at the emergent level or the extraordinary level and prescription information not having a determined medicine transporting destination are loaded onto the medicine transporting handcart 180 at the priority exit.

The display content of the information display 150 for an occasion where the container 140 corresponding to prescription information at the regular level for a determined transporting destination is loaded onto the medicine transporting handcart 180 at the regular exit will be discussed in detail below.

When the container 140 containing medicines is loaded onto the medicine transporting handcart 180 disposed at the regular exit, and if the medicine transporting handcart 180 at the regular exit is empty, a text indicating the determined medicine transporting destination, e.g. "AWARD", is displayed in the field for the transporting destination indication 154 of the information display 150 of the medicine transporting handcart 180 at the regular exit when the container 140 is loaded onto the medicine transporting handcart 180. If the medicine transporting handcart 180 at the regular exit is not empty, in contrast, a comparison is made between the medicine transporting destination of the container 140 that is about to be loaded and the medicine transporting destination of the container 140 which has been loaded earlier. If the medicine transporting destinations match each other, the container 140 is loaded onto the medicine transporting handcart 180 at the regular exit. If not, however, the container 140 is loaded onto the medicine transporting handcart 180 at the priority exit to prevent mixed loading.

In this way, the containers 140 are loaded one after another onto the medicine transporting handcart 180 at the regular exit. It is assumed that all the containers 140 for the same medicine transporting destination can be accommodated in one medicine transporting handcart 180 (see FIG. 11A). For example, it is assumed that 10 containers 140 are actually accommodated in a medicine transporting handcart 180 capable of accommodating up to 27 containers 140. Then, a text indicating that the loading order of the medicine transporting handcart 180 is the first and that there is no following medicine transporting handcart 180, e.g. "CART 1/1", is displayed in the field for the handcart information indication 155 of the information display 150 of the medicine transporting handcart 180. A text indicating the number of the containers 140 actually loaded on the medicine transporting handcart 180 and the maximum number of containers 140 that can be loaded on the medicine transporting handcart 180, e.g. "TRAY 10/27", is displayed in the field for the container information indication 156. Because there is no distributed loading for any patient, the field for the distribution information indication 157 is cleared into blank display, for example.

It is assumed that there are a large number of containers 140 for the same medicine transporting destination, "A WARD". For example, it is assumed that the number of the containers 140 is 45, which exceeds 27, the maximum number of containers 140 that can be loaded on one medicine transporting handcart 180. Then, the containers 140 cannot be accommodated in one medicine transporting handcart 180, and are distributedly loaded onto two medicine transporting handcarts 180. In this case (see FIGS. 11B and 11C), the maximum loadable number, 27, of containers 140 are loaded onto the first medicine transporting handcart 180, and the remaining 18 containers 140 are loaded onto the second medicine transporting handcart 180. On an information display 150a of the first medicine transporting handcart 180, a text indicating that the loading order of the medicine transporting handcart 180 is the first and that there is a following, second medicine transporting handcart 180, e.g. "CART 1/2", is displayed in the field for the handcart information indication 155. A text indicating the number of the containers 140 actually loaded on the medicine transporting handcart 180 and the maximum number of containers 140 that can be loaded on the medicine transporting handcart 180, e.g. "TRAY 27/27", is displayed in the field for the container information indication 156. If there is no distributed loading for any patient, the field for the distribution information indication 157 is cleared.

On an information display 150b of the second medicine transporting handcart 180, meanwhile, a text indicating that the loading order of the medicine transporting handcart 180 is the second and that there is no following medicine transporting handcart 180 and the second medicine transporting handcart 180 is the last, e.g. "CART 2/2", is displayed in the field for the handcart information indication 155. A text indicating the number of the containers 140 actually loaded on the medicine transporting handcart 180 and the maximum number of containers 140 that can be loaded on the medicine transporting handcart 180, e.g. "TRAY 18/27", is displayed in the field for the container information indication 156. If there is no distributed loading for any patient, the field for the distribution information indication 157 is cleared.

It is assumed that only one of a plurality of containers 140, e.g. three containers 140, for one patient is loaded onto the first medicine transporting handcart 180 and the remaining two containers 140 are loaded onto the second medicine transporting handcart 180 (see FIG. 11D). Then, according to such distributed loading for one patient, a text indicating the numerator and the total number, "1/3", is displayed along with the patient name in the field for the distribution information indication 157 of the information display 150a. A text indicating the numerator and the total number, "2/3", is displayed along with the patient name in the field for the distribution information indication 157 of the information display 150b.

Further, although not shown, it is assumed that there are much more containers 140 for the same medicine transporting destination. For example, it is assumed that there are 66 containers 140, which are distributedly loaded onto three medicine transporting handcarts 180. Then, on the information display 150 of the first medicine transporting handcart 180, a text "CART 1/3" is displayed in the field for the handcart information indication 155. A text "TRAY 27/27" is displayed in the field for the container information indication 156. On the information display 150 of the third medicine transporting handcart 180, a text "CART 2/3" is displayed in the field for the handcart information indication 155. A text "TRAY 27/27" is displayed in the field for the container information indication 156. On the information display 150 of the second medicine transporting handcart 180, a text "CART 3/3" is displayed in the field for the handcart information indication 155. A text "TRAY 12/27" is displayed in the field for the container information indication 156.

If the total number of containers 140 for the same medicine transporting destination, and thus the total number, e.g. "3", of medicine transporting handcarts 180 for the same medicine transporting destination, is immediately found because prescription information is already accumulated or prescription information is immediately accumulated, a text "CART 1/3" may be displayed in the field for the handcart information indication 155 of the information display 150 of the first medicine transporting handcart 180. Even if prescription information is not accumulated in time for completion of loading onto the first medicine transporting handcart 180, a text in the field for the handcart information indication 155 of the information display 150 of the first medicine transporting handcart 180 may be rewritten from "CART 1/2" to "CART 1/3" if the information display 150 is in the accessible range of the wireless transmitter or moved into the accessible range upon request.

In this way, the medicine transporting handcart 180 may be commonly used among transporting destinations. A conveying person who pushes the medicine transporting handcart 180 by hand to move the medicine transporting handcart 180 to a medicine transporting destination and an administering person who arranges medicines at a medicine transporting destination can perform his/her operation with ease and accuracy. That is, each person sees the information display 150 attached to the medicine transporting handcart 180 to read the display content of the information display 150 with his/her eyes to easily grasp and confirm the transporting destination. In addition, each person can see the information display 150 attached to the medicine transporting handcart 180 with his/her eyes to easily grasp whether there is only one medicine transporting handcart 180, or there are a plurality of medicine transporting handcarts 180, to be moved to the same location, and if there are a plurality, identify such medicine transporting handcarts 180. Further, even if medicines to be administered to one patient are contained in a plurality of containers 140 which are distributedly loaded onto a plurality of medicine transporting handcarts 180, it is easy to grasp not only the patient name identifying the patient relevant to the distributed loading but also the distribution status of the distributedly loaded containers 140.

In the embodiment described above, the dedicated container feeding device 121 is provided at the most upstream position of the container conveying path. However, the container feeding device 121 is not necessarily independently provided. The container loading device 170 may also serve as the container feeding device (see Patent Document 1, for example), or the container feeding device may be incorporated into any of the automated medicine dispensing apparatuses 110 or distributed to several automated medicine dispensing apparatuses 110.

In the embodiment described above, the dispensation control device 160 is provided at the operating table 120. However, the location of installation of the dispensation control device 160 is not limited, and any of centralized control and distributed control may be used. For example, the dispensation control device 160 configured to control cooperation among the container feeding device 121, the automated medicine dispensing apparatuses 110, and the container loading device 170 may not be provided with an information processing function and a control function for causing the information display 150 to display the indications 154 to 157, and such functions may be provided by other devices. In this case, the operating table 120 can be dispensed with.

In the embodiment described above, the information display 150 is accessed through radio communication. However, the method of access to the information display 150 is not limited to radio communication, and the information display 150 may be accessed through optically communication or contact transfer, for example.

In the description of the embodiment shown in FIGS. 9 to 11, it is presumed that the system shown in FIGS. 9 to 11 is used together with the system shown in FIGS. 1 to 8. As a matter of course, however, the system shown in FIGS. 9 to 11 may be separated from the system shown in FIGS. 1 to 8 so that the system shown in FIGS. 9 to 11 can be implemented independently.

The invention claimed is:

1. A medicine dispensing system comprising:
 a plurality of containers each provided with a first information display having a communication function and including a display portion for displaying rewritable information in a visibly recognizable manner;
 a container conveying mechanism operable to convey the plurality of containers;
 a medicine dispenser provided to face a conveying path of the container conveying mechanism;
 a medicine transporting vehicle capable of conveying the plurality of containers and provided with a second information display having a communication function and including a display portion for displaying rewritable information in a visibly recognizable manner;
 a container loading device operable to load the plurality of containers onto the medicine transporting vehicle; and
 a dispensation control device operable to transmit display information to the first information display based on pharmaceutical indication data so as to cause the information to be displayed on the display portion of the first information display, and operable to output to the container conveying mechanism and the medicine dispenser a command for controlling cooperation between the container conveying mechanism and the medicine dispenser based on pharmaceutical indication data so as to cause one or more sorts of indicated medicines to be dispensed from the medicine dispenser to the container, and further operable to give a load command to the container loading device to indicate a medicine transporting destination based on information indicating the medicine transporting destination, and operable to transmit display information to the second information display based on information indicating the medicine transporting destination so as to cause at least information on the medicine transporting destination and whether or not a following medicine transporting vehicle is present to be displayed on the display portion of the second information display, wherein:
 the medicine dispenser is configured to notify the dispensation control device of information on stockout medicine if any;
 the dispensation control device is configured to transmit a write command to the first information display upon receipt of the information on stockout medicine from the medicine dispenser so as to cause the information on stockout medicine to be displayed on the display portion of the first information display in the visibly recognizable manner; and
 the dispensation control device further comprises:
 matching data storing means for storing medicine—sub container matching data on matching between a plurality of sorts of medicines and sub containers capable of containing such medicines;
 computing means for determining planar arrangement of the sub containers in the container with reference to the medicine—sub container matching data to dispose in an internal space of the container the one or more sub containers containing the one or more sorts of medicines indicated by the pharmaceutical indication data and to partition the internal space of the container; and
 display instructing means for transmitting partition information on the planar arrangement determined by the computing means to the first information display so as to cause the determined planar arrangement to be displayed on the display portion of the first information display.

2. A medicine dispensing system comprising:
 a container provided with an information display having a communication function and including a display portion for displaying rewritable information in a visibly recognizable manner;
 a container conveying mechanism operable to convey the container;
 a medicine dispenser provided to face a conveying path of the container conveying mechanism; and
 a dispensation control device operable to transmit display information to the information display based on pharmaceutical indication data so as to cause the information to be displayed on the display portion, and operable to output to the container conveying mechanism and the medicine dispenser a command for controlling cooperation between the container conveying mechanism and the medicine dispenser based on pharmaceutical indication data so as to cause one or more sorts of indicated medicines to be dispensed from the medicine dispenser to the container, wherein:
 the medicine dispenser is configured to notify the dispensation control device of information on stockout medicine if any;
 the dispensation control device is configured to transmit a write command to the information display upon receipt of the information on stockout medicine from the medicine dispenser so as to cause the information on stockout medicine to be displayed on the display portion in the visibly recognizable manner; and
 the dispensation control device further comprises:
 matching data storing means for storing medicine—sub container matching data on matching between a plurality of sorts of medicines and sub containers capable of containing such medicines;
 computing means for determining planar arrangement of the sub containers in the container with reference to the medicine—sub container matching data to dispose in an internal space of the container the one or more sub containers containing the one or more sorts of medicines indicated by the pharmaceutical indication data and to partition the internal space of the container; and
 display instructing means for transmitting partition information on the planar arrangement determined by the computing means to the information display so as to cause the determined planar arrangement to be displayed on the display portion.

3. The medicine dispensing system according to claim 1, wherein
the display instructing means displays the planar arrangement in a field for the stockout information in the display portion by overwriting the stockout information with the planar arrangement.

4. A medicine dispensing system comprising:
a container provided with an information display having a communication function and including a display portion for displaying rewritable information in a visibly recognizable manner;
a container conveying mechanism operable to convey the container;
a medicine dispenser provided to face a conveying path of the container conveying mechanism; and
a dispensation control device operable to transmit display information to the information display based on pharmaceutical indication data so as to cause the information to be displayed on the display portion, and operable to output to the container conveying mechanism and the medicine dispenser a command for controlling cooperation between the container conveying mechanism and the medicine dispenser based on pharmaceutical indication data so as to cause one or more sorts of indicated medicines to be dispensed from the medicine dispenser to the container, wherein:
the medicine dispenser is configured to notify the dispensation control device of information on stockout medicine if any; and
the dispensation control device is configured to transmit a write command to the information display upon receipt of the information on stockout medicine from the medicine dispenser so as to cause the information on stockout medicine to be displayed on the display portion in the visibly recognizable manner.

5. The medicine dispensing system according to claim 1, wherein
the stockout information includes text information that describes a stockout status.

6. The medicine dispensing system according to claim 1, wherein
the stockout information includes the name and the quantity of a stockout medicine.

7. A medicine dispensing system comprising:
a medicine dispenser operable to contain a medicine and feed the medicine to a plurality of containers;
a medicine transporting vehicle capable of conveying the plurality of containers and provided with an information display having a communication function and including a display portion for displaying rewritable information in a visibly recognizable manner;
a container loading device operable to load the plurality of containers onto the medicine transporting vehicle; and
a dispensation control device operable to give a load command to the container loading device based on information indicating a medicine transporting destination, and operable to transmit display information to the information display based on information indicating a medicine transporting destination so as to cause at least information on the medicine transporting destination, a loading order, and whether or not a following medicine transporting vehicle is present to be displayed on the display portion of the information display.

8. The medicine dispensing system according to claim 7, wherein
the dispensation control device generates the load command based on information identifying the medicine transporting destination such that the containers for the same medicine transporting destination are not mixedly loaded with the containers for a different destination, and such that the containers for the same medicine transporting destination are loaded onto one medicine transporting vehicle if the one medicine transporting vehicle can accommodate all of such containers, and otherwise onto a plurality of medicine transporting vehicles.

9. The medicine dispensing system according to claim 8, wherein
if a plurality of the containers for the same medicine transporting destination are loaded distributedly onto a plurality of the medicine transporting vehicles, the dispensation control device determines, based on prescription information or other information identifying a subject patient, whether or not a plurality of the containers containing medicines to be prescribed for the same patient are loaded distributedly onto a plurality of the medicine transporting vehicles, and causes the information displays of the medicine transporting vehicles for respective medicine transporting destinations to display distribution information indicating the patient relevant to the distributed loading and a distribution status of the distributedly loaded containers.

10. The medicine dispensing system according to claim 2, wherein
the display instructing means displays the planar arrangement in a field for the stockout information in the display portion by overwriting the stockout information with the planar arrangement.

11. The medicine dispensing system according to claim 2, wherein
the stockout information includes text information that describes a stockout status.

12. The medicine dispensing system according to claim 2, wherein
the stockout information includes the name and the quantity of a stockout medicine.

13. The medicine dispensing system according to claim 3, wherein
the stockout information includes text information that describes a stockout status.

14. The medicine dispensing system according to claim 3, wherein
the stockout information includes the name and the quantity of a stockout medicine.

15. The medicine dispensing system according to claim 4, wherein
the stockout information includes text information that describes a stockout status.

16. The medicine dispensing system according to claim 4, wherein
the stockout information includes the name and the quantity of a stockout medicine.

* * * * *